United States Patent
Lodge et al.

Patent Number: 5,993,432
Date of Patent: *Nov. 30, 1999

[54] WEB MATERIALS HAVING ELASTIC-LIKE AND EXPANSIVE ZONES

[75] Inventors: Richard W. Lodge; John J. Curro, both of Cincinnati, Ohio

[73] Assignee: The Procter & Gamble Company, Cincinnati, Ohio

[*] Notice: This patent is subject to a terminal disclaimer.

[21] Appl. No.: 08/931,019

[22] Filed: Sep. 15, 1997

Related U.S. Application Data

[63] Continuation of application No. 08/566,471, Dec. 4, 1995, abandoned.

[51] Int. Cl.$^6$ .................................................. A61F 13/15
[52] U.S. Cl. ........................... 604/385.2; 604/385.1
[58] Field of Search .............................. 604/367, 386, 604/385.1, 385.2

[56] References Cited

U.S. PATENT DOCUMENTS

| | | |
|---|---|---|
| 235,449 | 12/1880 | Newton . |
| 659,266 | 10/1900 | Stewart . |
| 728,828 | 5/1903 | Arkell . |
| 782,977 | 2/1905 | Madden . |
| 1,507,949 | 9/1924 | Angier . |
| 1,582,842 | 4/1926 | Lorenz . |
| 2,007,047 | 7/1935 | Gibbs . |
| 2,158,929 | 5/1939 | Dunajeff . |
| 2,177,490 | 10/1939 | Kieffer . |
| 2,257,428 | 9/1941 | Ruegenberg . |
| 2,679,887 | 6/1954 | Doyle et al. . |
| 2,896,692 | 7/1959 | Villoresi . |
| 2,901,951 | 9/1959 | Hochfeld . |
| 2,974,716 | 3/1961 | Fourness . |
| 3,151,947 | 10/1964 | Hastings . |
| 3,236,718 | 2/1966 | Chohn et al. . |
| 3,313,080 | 4/1967 | Gewiss . |
| 3,351,441 | 11/1967 | Gewiss . |
| 3,362,118 | 1/1968 | Brunner . |
| 3,542,634 | 11/1970 | Such et al. . |
| 3,550,423 | 12/1970 | Gewiss . |
| 3,726,408 | 4/1973 | Gewiss . |
| 3,817,827 | 6/1974 | Benz . |
| 3,828,784 | 8/1974 | Zoephel . |
| 3,843,761 | 10/1974 | Bierenbaum et al. . |
| 3,860,003 | 1/1975 | Buell . |
| 3,894,352 | 7/1975 | Hooker . |
| 3,929,135 | 12/1975 | Thompson . |
| 3,969,473 | 7/1976 | Meek . |
| 3,975,455 | 8/1976 | Falender et al. . |
| 3,992,162 | 11/1976 | Gewiss . |
| 4,082,877 | 4/1978 | Shadle . |
| 4,101,625 | 7/1978 | Haley . |
| 4,104,430 | 8/1978 | Fenton . |
| 4,110,391 | 8/1978 | Berzen et al. . |
| 4,153,664 | 5/1979 | Sabee . |

(List continued on next page.)

FOREIGN PATENT DOCUMENTS

| | | |
|---|---|---|
| 0 307 871 B1 | 12/1992 | European Pat. Off. . |
| WO 93/25171 | 12/1991 | WIPO . |
| WO 95/08311 | 3/1995 | WIPO . |
| WO 95/20931 | 8/1995 | WIPO . |

*Primary Examiner*—John G. Weiss
*Assistant Examiner*—Dennis Ruhl
*Attorney, Agent, or Firm*—Steven W. Miller; Kevin C. Johnson; Jacobus C. Rasser

[57] ABSTRACT

A web material exhibiting both an elastic-like and an expansive behavior in response to an applied elongation. The web material includes an elastic-like zone and an expansive zone disposed adjacent to the elastic-like zone. The expansive zone allows the elastic-like zone to extend without generating excessive tensional forces. The elastic-like zone includes a strainable network having a first region and a second region. The second region has a surface-pathlength greater than the surface-pathlength of the first region. The expansive zone has a surface-pathlength greater than the first region and different than that of the second region.

10 Claims, 9 Drawing Sheets

U.S. PATENT DOCUMENTS

| | | |
|---|---|---|
| 4,321,924 | 3/1982 | Ahr . |
| 4,324,246 | 4/1982 | Mullane et al. . |
| 4,342,314 | 8/1982 | Radel et al. . |
| 4,425,130 | 1/1984 | DesMarais . |
| 4,463,045 | 7/1984 | Ahr et al. . |
| 4,554,121 | 11/1985 | Kramers . |
| 4,589,876 | 5/1986 | Van Tilburg . |
| 4,609,518 | 9/1986 | Curro et al. . |
| 4,617,241 | 10/1986 | Mueller . |
| 4,640,859 | 2/1987 | Hansen et al. . |
| 4,719,261 | 1/1988 | Bunnelle et al. . |
| 4,780,344 | 10/1988 | Hoberman . |
| 4,834,741 | 5/1989 | Sabee . |
| 4,950,264 | 8/1990 | Osborn . |
| 4,968,313 | 11/1990 | Sabee . |
| 5,006,394 | 4/1991 | Baird . |
| 5,008,140 | 4/1991 | Schmertz . |
| 5,028,474 | 7/1991 | Czaplicki . |
| 5,034,078 | 7/1991 | Hodgson, Jr. et al. . |
| 5,125,918 | 6/1992 | Seidy . |
| 5,143,774 | 9/1992 | Cancio et al. . |
| 5,151,092 | 9/1992 | Buell et al. . |
| 5,196,000 | 3/1993 | Clear et al. . |
| 5,202,173 | 4/1993 | Wu et al. . |
| 5,209,801 | 5/1993 | Smith . |
| 5,234,422 | 8/1993 | Sneller et al. . |
| 5,254,111 | 10/1993 | Cancio et al. . |
| 5,268,213 | 12/1993 | Murakami et al. . |
| 5,296,184 | 3/1994 | Wu et al. . |
| 5,344,416 | 9/1994 | Niihara ................. 604/385.1 |
| 5,344,691 | 9/1994 | Hanschen et al. . |
| 5,389,094 | 2/1995 | Lavash et al. ........ 604/385.2 |
| 5,422,178 | 6/1995 | Swenson et al. . |
| 5,518,801 | 5/1996 | Chappell et al. ............ 428/152 |
| 5,520,674 | 5/1996 | Lavon et al. ........... 604/385.2 |
| 5,542,942 | 8/1996 | Kline et al. ............ 604/385.2 |

WEB MATERIALS HAVING ELASTIC-LIKE AND EXPANSIVE ZONES

This is a continuation of application Ser. No. 08/566,471, filed on Dec. 4, 1995 now abandoned.

FIELD OF THE INVENTION

The present invention relates to web materials, and more particularly, to such web materials having elastic-like and expansive zones. Web materials of the present invention having elastic-like and expansive zones exhibit an elastic-like behavior in response to an applied and subsequently released (i.e., cycled) elongation along at least one axis.

Web materials of the present invention have a wide range of potential uses in both durable and disposable articles, but are particularly well suited for use in disposable absorbent articles such as disposable diapers, incontinent briefs, incontinent undergarments, training pants, feminine hygiene garments, and the like.

BACKGROUND OF THE INVENTION

Infants and other incontinent individuals wear absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art. For example, U.S. Pat. No. Re. 26,152, entitled "Disposable Diaper", issued to Duncan and Baker on Jan. 31, 1967, describes a disposable diaper which has achieved wide acceptance and commercial success. U.S. Pat. No. 3,860,003, entitled "Contractible Side Portions For Disposable Diaper", issued to Buell on Jan. 14, 1975, describes an elasticized leg cuff disposable diaper which has achieved wide acceptance and commercial success.

However, absorbent articles have a tendency to sag or gap away from and to slide/slip down on the body of the wearer during wear. This sagging/gapping and sliding/slipping is caused by the relative motions of the wearer as the wearer breathes, moves and changes positions, by the downward forces generated when the absorbent is loaded with body exudates, and by the materials of the absorbent article itself when subjected to such wearer's motions. This sagging/gapping and sliding/slipping of the absorbent article can lead to premature leakage and poor fit of the absorbent article about the wearer in the waist regions and the leg regions of the absorbent article.

In order to more snugly fit absorbent articles about the wearer, certain commercially available absorbent articles have been provided with elastic features. An example of a disposable diaper with elastic side panels is disclosed in U.S. Pat. No. 5,151,092, entitled "Absorbent Article With Dynamic Elastic Waist Feature Having Predisposed Flexural Hinge", issued to Buell, Clear, and Falcone on Sept. 22, 1992. However, elastics are costly and require a certain degree of manipulation and handling during assembly. Further, while elastics do provide a degree of stretch for the absorbent article, the components of the absorbent article to which the elastics are attached are typically not elastic such that the elastics must be prestretched prior to being secured to the absorbent article or the inelastic components must be subjected to mechanical stretching (e.g., ring rolling) to enable the added elastic to be effective. Otherwise, the added elastic is restrained by the inelastic components.

Therefore, it is an object of the present invention to provide relatively low cost, easy to manufacture, web materials which exhibit an "elastic-like" behavior in response to an applied and subsequently released elongation. As used herein, the term "elastic-like" describes the behavior of web materials which when subjected to an applied elongation, the web materials extend in the direction of applied elongation and when the applied elongation is released the web materials return, to a substantial degree, to their untensioned condition.

It is a further object of the present invention to provide a relatively low cost, easy to manufacture, absorbent article having sustained dynamic fit about the wearer during use.

It is a further object of the present invention to provide an absorbent article having a unique extensible waist feature, preferably without the use of elastic, that provides sustained dynamic fit and improved resistance to leakage during use due to the conformability of the materials forming the waist feature by virtue of their readily extensible nature.

These and other objects of the present invention will be more readily apparent when considered in reference to the following description and when taken in conjunction with the accompanying drawings.

SUMMARY OF THE INVENTION

The present invention provides a web material which exhibits an elastic-like behavior in response to an applied and subsequently released elongation without the use of elastic materials such as natural or synthetic rubber. Web materials of the present invention have an elastic-like zone and an adjacent expansive zone.

The elastic-like zone is intended to elastically expand and contract. The elastic-like zone preferably comprises a structural elastic-like film (SELF) web, since a SELF web allows the force/extension characteristics to be specifically designed with a minimum amount of materials (no elastic materials need to be used.)

A SELF web exhibits an elastic-like behavior in the direction of elongation without the use of added elastic materials. SELF webs exhibit at least two significantly different stages of controlled resistive force to elongation along at least one predetermined axis when subjected to an applied elongation in a direction parallel to the predetermined axis. SELF webs include a strainable network having at least two contiguous, distinct, and dissimilar regions. One of the regions is configured so that it will exhibit resistive forces in response to the applied elongation in a direction parallel to the predetermined axis before a substantial portion of the other region develops significant resistive forces to the applied elongation. At least one of the regions has a surface-pathlength which is greater than that of the other region as measured substantially parallel to the predetermined axis when the material is in an untensioned condition. The region exhibiting the longer surface-pathlength includes one or more rib-like elements which extend beyond the plane of the other region. SELF webs exhibit first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region.

SELF webs may also exhibit an elongation and recovery with a definite and sudden increase in the force resisting elongation where this definite and sudden increase in resistive force restricts further elongation against relatively small elongation forces. The definite and sudden increase in the force resisting elongation is referred to as a "force wall". As used herein, the term "force wall" refers to the behavior of the resistive force of a web material during elongation wherein at some point in the elongation, distinct from the untensioned or starting point, the force resisting the applied elongation suddenly increases. After reaching the force wall, additional elongation of the web material is only accomplished via an increase in the elongation force to overcome the higher resistive force of the web material.

The rib-like elements allow the second region to undergo a substantially "geometric deformation" which results in significantly less resistive forces to an applied elongation than that exhibited by the "molecular-level deformation" of the first region. As used herein, the term "molecular-level deformation" refers to deformation which occurs on a molecular level and is not discernible to the normal naked eye. That is, even though one may be able to discern the effect of molecular-level deformation, e.g., elongation of the web material, one is not able to discern the deformation which allows or causes it to happen. This is in contrast to "geometric deformation". As used herein the term "geometric deformation" refers to deformations which are discernible to the normal naked eye when the web material or articles embodying the web material are subjected to an applied elongation. Types of geometric deformation include, but are not limited to bending, unfolding, and rotating.

The expansive zone, disposed adjacent to the elastic-like zone, allows the elastic-like zone to extend without generating any excessive tensional forces. The expansive zone is preferably subjected to mechanical stretching at least to a degree to be extensible (i.e., the material making up the expansive zone has been pre-strained or permanently elongated). Without the expansive zone disposed adjacent the elastic-like zone, the tensional forces would be concentrated along a line extending adjacent the elastic-like zone which would substantially inhibit the expansion of the elastic-like zone.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numerals identify like elements and wherein:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). Because of their single use nature, low cost materials and methods of construction are highly desirable in disposable absorbent articles. A "unitary" absorbent article refers to absorbent articles which are formed of separate parts united together to form a coordinated entity so that they do not require separate manipulative parts like a separate holder and liner.

Figure 1:
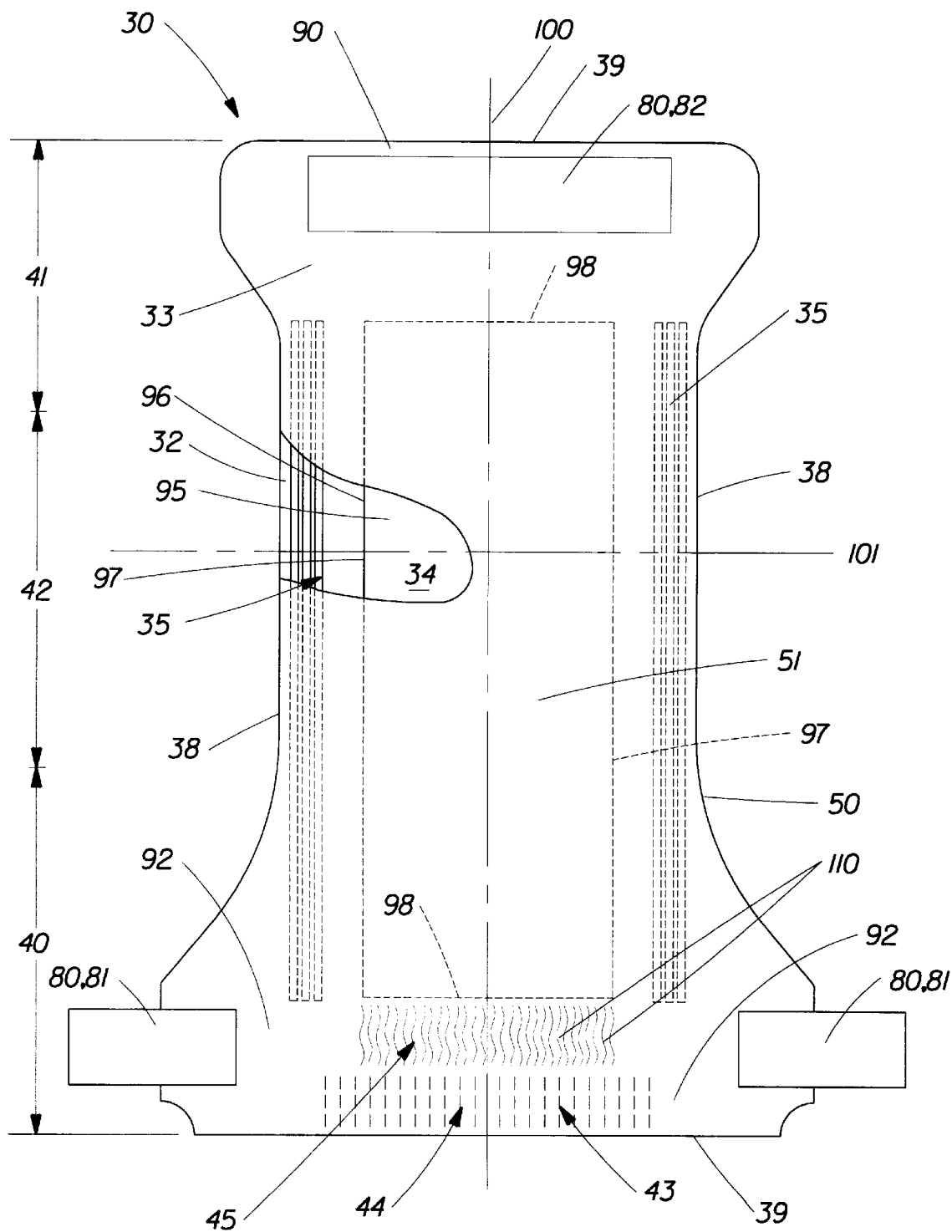
FIG. 1 is a plan view of a disposable diaper embodiment of the present invention having portions cut-away to reveal underlying structure, the outer surface of the diaper facing the viewer.

A preferred embodiment of an absorbent article of the present invention is the unitary disposable absorbent article, diaper 30, shown in FIG. 1. As used herein, the term "diaper", refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, training pants, and the like.

FIG. 1 is a plan view of a disposable diaper 30 of the present invention in its flat-out, uncontracted state (i.e., with elastic induced contraction pulled out) with portions of the structure being cut-away to more clearly show the construction of the diaper 30 and with the portion of the diaper 30 which faces away from the wearer, i.e., the outer surface, facing the viewer. As shown in FIG. 1, the diaper 30 comprises a liquid pervious topsheet 32, a liquid impervious backsheet 33 joined with the topsheet 32, an absorbent core 34 positioned between the topsheet 32 and the backsheet 33, elasticized leg cuffs 35, an extensible back waist feature 43 comprising an elastic-like zone 44 and an expansive zone 45, a front waist feature 90, ear flaps 92, and a fastening system 80 comprising a pair of first fastening members 81 and a second fastening member 82.

While the diaper 30 may be assembled in a variety of well known configurations, preferred diaper configurations are described generally in U.S. Pat. No. 3,860,003, issued to Kenneth B. Buell on Jan. 14, 1975; and U.S. Pat. No. 5,151,092 issued to Kenneth B. Buell et al. on Sept. 29, 1992. Each of these patents are hereby incorporated herein by reference.

The diaper 30 is shown in FIG. 1 to have an inner surface 50, an outer surface 51 (facing the viewer in FIG. 1) opposed to the inner surface, a first waist region 40, a second waist region 41 opposed to the first waist region 40, a crotch region 42 positioned between the first waist region 40 and the second waist region 41, and a periphery which is defined by the outer perimeter or edges of the diaper 30 in which the longitudinal edges are designated 38 and the end edges are designated 39. The inner surface 50 of the diaper comprises that portion of the diaper 30 which is positioned adjacent to the wearer's body during use (i.e., the inner surface 50 is generally formed by at least a portion of the topsheet 32 and other components joined to the topsheet 32). The outer surface 51 comprises that portion of the diaper 30 which is positioned away from the wearer's body (i.e., the outer surface 51 is generally formed by at least a portion of the backsheet 33 and other components joined to the backsheet 33). As used herein, the term "joined" encompasses configurations whereby an element is directly secured to the other element by affixing the element directly to the other element, and configurations whereby the element is indirectly secured to the other element by affixing the element to intermediate members(s) which in turn are affixed to the other element. The first waist region 40 and the second waist region 41 extend, respectively, from the end edges 39 of the periphery to the crotch region 42. The lateral direction (x direction or width) is defined as the direction parallel to the lateral centerline 101 of the diaper 30; the longitudinal direction (y direction or length) is defined as the direction parallel to the longitudinal centerline 100; and the axial direction (z direction or thickness) is defined as the direction extending through the thickness of the diaper 30.

The absorbent core 34 may be any absorbent member which is generally compressible, conformable, non-irritating to the wearer's skin, and capable of absorbing and retaining liquids such as urine and other certain body exudates. The absorbent core 34 has an outer surface 95, an inner surface 96, side edges 97, and waist edges 98. The absorbent core 34 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 34 may vary (e.g., the absorbent core may have varying caliper zones, a hydrophilic gradient, a superabsorbent gradient, or lower average density and lower average basis weight acquisition zones; or may comprise one or more layers or structures). However, the total absorbent capacity of the absorbent core 34 should be compatible with the design loading and the intended use of the diaper 30. The size and absorbent capacity of the absorbent core 34 may also be varied to accommodate wearers ranging from infants through adults.

One embodiment of the diaper 30 has asymmetric, modified T-shaped, absorbent core 34 having ears in the first waist region 40 but a generally rectangular shape in the second waist region 41. Exemplary absorbent structures for use as the absorbent core 34 of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing acquisition/distribution core of chemically stiffened fibers positioned over the absorbent storage cores as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The backsheet 33 is positioned adjacent the outer surface of the absorbent core 34 and is preferably joined thereto by attachment means (not shown) such as those well known in the art. For example, the backsheet 33 may be secured to the absorbent core 34 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 33 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 33 prevents the exudates absorbed and contained in the absorbent core 34 from wetting articles which contact the diaper 30 such as bedsheets and undergarments. Further, the backsheet 33 may permit vapors to escape from the absorbent core 34 (i.e., breathable) while still preventing exudates from passing through the backsheet 33. Thus, the backsheet 33 may comprise a woven or nonwoven material, polymeric films such as thermoplastic films of polyethylene or polypropylene, or composite materials such as a film-coated nonwoven material. An example of a suitable backsheet is a thermoplastic film having a thickness of from about 0.012 mm (0.5 mil) to about 0.051 mm (2.0 mils). Other suitable materials for the backsheet 33 include RR8220 blown films and RR5475 cast films as manufactured by Tredegar Industries, Inc. of Terre Haute, Ind. The backsheet 33 is preferably embossed and/or matte finished to provide a more clothlike appearance.

The topsheet 32 is positioned adjacent the inner surface of the absorbent core 34 and is preferably joined thereto and to the backsheet 33 by attachment means (not shown) such as those well known in the art. Suitable attachment means are described with respect to joining the backsheet 33 to the absorbent core 34. In a preferred embodiment of the present invention, the topsheet 32 and the backsheet 33 are joined directly to each other in the diaper periphery and are indirectly joined together by directly joining them to the absorbent core 34 by the attachment means (not shown).

The topsheet 32 is compliant, soft feeling, and non-irritating to the wearer's skin. Further, the topsheet 32 is preferably liquid pervious permitting liquids (e.g., urine) to readily penetrate through its thickness. A suitable topsheet 32 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 32 is preferably made of a hydrophobic material to isolate the wearer's skin from liquids which have passed through the topsheet 32 and are contained in the absorbent core 34 (i.e. to prevent rewet). If the topsheet 32 is made of a hydrophobic material, at least the upper surface of the topsheet 32 is treated to be hydrophilic so that liquids will transfer through the topsheet more rapidly. This diminishes the likelihood that body exudates will flow off the topsheet 32 rather than being drawn through the topsheet 32 and being absorbed by the absorbent core 34. The topsheet 32 can be rendered hydrophilic by treating it with a surfactant. Suitable methods for treating the topsheet 32 with a surfactant include spraying the topsheet 32 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

There are a number of manufacturing techniques which may be used to manufacture the topsheet 32. For example, the topsheet 32 may be a nonwoven web of fibers. When the topsheet 32 comprises a nonwoven web, the web may be spunbonded, carded, wet-laid, melt-blown, hydroentangled, combinations of the above, or the like. A suitable topsheet 32 is carded and thermally bonded by means well known to those skilled in the fabrics art. A satisfactory topsheet 32 comprises staple length polypropylene fibers having a denier of about 2.2. As used herein, the term "staple length fibers" refers to those fibers having a length of at least about 15.9 mm (0.625 inches). Preferably, the topsheet 32 has a basis weight from about 18 to about 25 grams per square meter. A suitable topsheet is manufactured by Veratec, Inc., a Division of International Paper Company, of Walpole, Mass. under the designation P-8.

The diaper 30 preferably further comprises elasticized leg cuffs 35 for providing improved containment of liquids and other body exudates. Each elasticized leg cuff 35 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. While each elasticized leg cuff 35 may be configured so as to be similar to any of the leg bands, side flaps, barrier cuffs, or elastic cuffs described above, each elasticized leg cuff 35 comprises a gasketing cuff as described in the above-referenced U.S. Pat. No. 3,860,003.

The diaper 30 further comprises an extensible back waist feature 43 that provides a more comfortable and contouring fit by initially conformably fitting the diaper to the wearer and sustaining this fit throughout the time of wear well past when the diaper has been loaded with exudates since the extensible back waist feature 43 allows the diaper to expand and contract. Further, the extensible back waist feature 43 develops and maintains wearing forces (tensions) that enhance the tensions developed and maintained by the closure system to maintain the diaper on the wearer and that enhance the fit of the diaper about the waist of the wearer. The extensible back waist feature 43 further provides more effective application of the diaper since even if the diaperer pulls one side of the extensible back waist feature farther than the other during application (asymmetrically), the diaper will "self-adjust" during wear.

As shown in FIG. 1, the extensible back waist feature 43 comprises an elastic-like zone 44 and an expansive zone 45. In the embodiment shown in FIG. 1, the elastic-like zone 44 extends longitudinally inwardly from the end edge 39 of the diaper 30 in the first waist region 40. The expansive zone 45 is joined to and extends longitudinally inwardly from the elastic-like zone 44. In the embodiment shown in FIG. 1, the expansive zone 45 extends both longitudinally inwardly from the waist edge 98 of the absorbent core 34 toward the centerline 101 and outwardly from the waist edge 98 of the absorbent core 34 toward the elastic-like zone 44. The term "izone" is used herein to denote an area or element of the waist feature or of the diaper. (While a zone is typically a distinct area or element, a zone may overlap somewhat with an adjacent zone.)

In the embodiment shown in FIG. 1, the elastic-like zone 44 comprises a structural elastic-like film (SELF) web comprising a portion of the backsheet 33. The elastically contractive and extensible behavior of the elastic-like zone 44 is derived from the backsheet without the need for added elastic material. The expansive zone 45 is unitary with the elastic-like zone 44 and also comprises a portion of the backsheet 33. Preferably, the expansive zone 45 is subjected to mechanical stretching at least to a degree to be extensible. The extension forces of the elastic-like zone 44 are higher than the extension forces of the adjacent expansive zone 45.

The elastic-like zone 44 is the primary component of the extensible back waist feature 43 that provides waist fit and appearance. (The elastic-like zone 44 may also be referred to as the waistband or waist panel of the back waist feature.) The elastic-like zone 44 is contiguous with the expansive zone 45 and is disposed longitudinally outwardly from the expansive zone 45 so as to fit in the lower back of the wearer. The elastic-like zone 44 is positioned toward the end edge 39 of the diaper 30 and preferably, forms at least a portion of the end edge 39 of the diaper 30. The elastic-like zone 44 maintains an area coverage, contacts the wearer in the lower back to snugly fit the wearer, and elastically expands and contracts, preferably in a direction having a vector component in the lateral direction, more preferably in the lateral direction, so as to dynamically move, fit, and conform to the wearer. It should be noted that the elastic-like zone 44 may elastically expand and contract in any other direction or in more than one direction.

The elastic-like zone 44 may take on a number of different sizes and shapes. Examples of suitable shapes for the elastic-like zone include arcuate, trapezoidal, triangular, etc. In a preferred embodiment such as shown in FIG. 1, the elastic-like zone has a rectangular shape.

The elastic-like zone 44 can be constructed of elements of the diaper such as the topsheet and/or the backsheet. For performance and cost reasons the elastic-like zone 44 preferably comprises a portion of the backsheet formed into a structural elastic-like film (SELF) web as described hereinafter. The term "web" herein refers to a sheet-like material comprising a single layer of material or a composite or a laminate of two or more layers.

In the embodiment of the present invention shown in FIG. 1, the extensible back waist feature 43 includes one elastic-like zone 44 and one expansive zone 45. However, diapers can be constructed to have multiple elastic-like zones and multiple expansive zones. For example, the diaper 30 can be constructed to also have an extensible front waist feature in the second waist region 41.

The expansive zone 45 is extensible in a direction having a vector component in substantially the same direction as the elastic-like zone. In the embodiment shown in FIG. 1, the expansive zone 45 is extensible in the lateral direction. It should be noted, however, that the expansive zone may be extensible in any other direction or in more than one direction. The expansive zone 45 is preferably positioned immediately adjacent to the elastic-like zone 44. The expansive zone 45 is designed to have lower extension forces than the elastic-like zone 44 up to a predetermined point. The expansive zone 45 is preferably subjected to mechanical stretching at least to a degree to be extensible (i.e., the material making up the expansive zone 45 is pre-strained or permanently elongated). The pre-straining of the expansive zone 45 allows the expansive zone to effectively elongate (yield) when the adjacent elastic-like zone 44 is extended, without generating any excessive tensional forces in the elastic-like zone 44. Without the expansive zone 45 disposed adjacent to the elastic-like zone 44, the tensional forces would be concentrated along a line extending adjacent to the elastic-like zone 44 which would inhibit the expansion of the elastic-like zone 44. Therefore, the diaper must be constructed so that the expansive zone does not restrict the designed expansion and contraction of the elastic-like zone.

The expansive zone 45 may take on a number of different sizes and shapes. For example, the expansive zone may have a trapezoidal, arcuate, or complex shape. As shown in FIG. 1, the expansive zone 45 preferably has a rectangular shape. The size of the expansive zone may also widely vary, depending upon the desired properties of the extensible back waist feature. The expansive zone 45 may extend longitudinally inwardly from the elastic-like zone 44 to the crotch region 42 to the lateral centerline 101, to the front waist feature 90, or the entire length of the diaper.

The expansive zone 45 can be constructed of elements of the diaper such as the backsheet and/or the topsheet. In the embodiment of the present invention shown in FIG. 1, the expansive zone 45 comprises a portion of the backsheet which has been prestrained or permanently elongated as described hereinafter.

Figure 2:
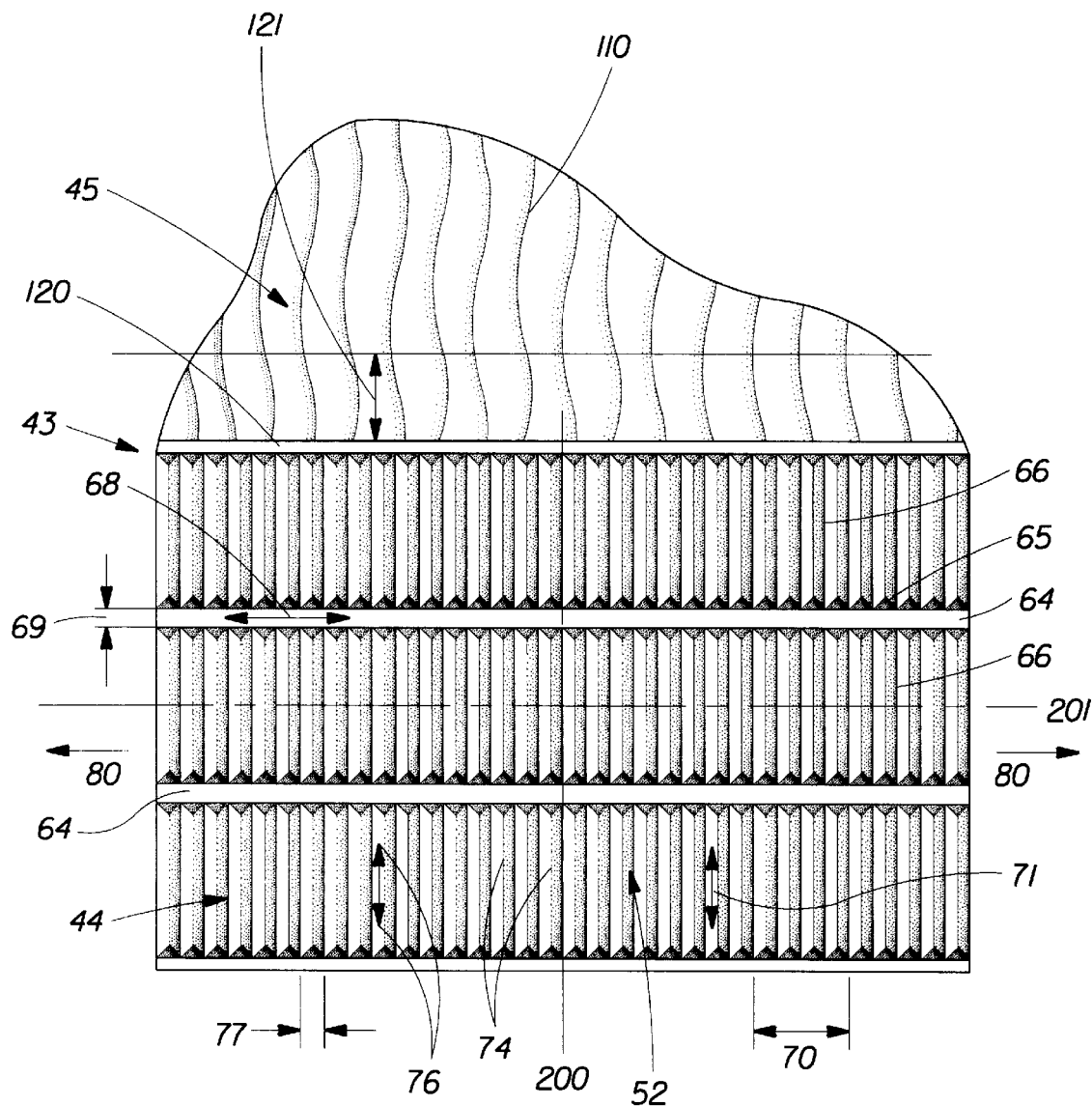
FIG. 2 is an enlarged, fragmentary plan view of the extensible back waist feature of the present invention showing the elastic-like zone and the expansive zone.

FIG. 2 is an enlarged, fragmentary plan view of the extensible back waist feature 43 showing the elastic-like zone 44 and the expansive zone 45. In the embodiment of the present invention shown in FIGS. 1 and 2, the extensible back waist feature comprises a portion of the backsheet. The backsheet 33 is preferably a web material constructed of a single layer of polymeric material. The web material is preferably comprised substantially of linear low density polyethylene (LLDPE), although it may also be comprised of other polyolefins such as polyethylenes including low density polyethylene (LDPE), ultra low density polyethylene (ULDPE), high density polyethylene (HDPE), or polypropylene and/or blends thereof and other materials. Examples of other suitable polymeric materials include, but are not limited to polyester, polyurethanes, compostable or biodegradable polymers, and breathable polymers.

The extensible back waist feature is shown in FIG. 2 in its substantially untensioned condition. The SELF web 52 forming the elastic-like zone 44 has two centerlines, a first centerline 201, (which is also referred to as an axis, line, or direction), and a second centerline 200, (which is also referred to as an axis, line, or direction), which is generally perpendicular to the first centerline 201.

The SELF web 52 includes a "strainable network" of distinct regions. As used herein, the term "strainable network" refers to an interconnected and interrelated group of regions which are able to be extended to some useful degree in a predetermined direction providing the SELF web with an elastic-like behavior in response to an applied and subsequently released elongation. The strainable network includes at least a first region 64 (also generally referred to herein as bands or channels) and a second region 66 (also generally referred to herein as ribs). The SELF web also includes a transitional region 65 which is at the interface between the first region 64 and the second region 66. The transitional region 65 will exhibit complex combinations of the behavior of both the first region and the second region. It is recognized that every embodiment of the present invention will have a transitional region, however, preferred embodiments of the present invention will exhibit elastic-like behavior substantially as a result of the first region 64 and the second regions 66. Therefore, the ensuing description of the present invention will be concerned with the behavior of the SELF web in the first regions and the second regions only and not the complex behavior of the SELF web in the transitional regions 65.

SELF web 52 has a first surface and a second surface. In the preferred embodiment shown in FIG. 2, the strainable network includes a plurality of first regions 64 and a plurality of second regions 66. The first regions 64 have a first axis 68 and a second axis 69, wherein the first axis 68 is preferably longer than the second axis 69. The first axis 68 of the first region 64 is substantially parallel to the first axis 201 of the SELF web 52, while the second axis 69 is substantially parallel to the second axis 200 of the SELF web 52. The second regions 66 have a first axis 70 and a second axis 71. The first axis 70 is substantially parallel to the first axis 201 of the SELF web 52, while the second axis 71 is substantially parallel to the second axis 200 of the SELF web 52. In the preferred embodiment of FIG. 2, the first regions 64 and the second regions 66 are substantially linear, extending continuously in a direction substantially parallel to the first axis of the SELF web 52.

The first region 64 has an elastic modulus E1 and a cross-sectional area A1. The second region 66 has a modulus E2 and a cross-sectional area A2.

In the illustrated embodiment, the SELF web 52 has been "formed" such that the SELF web 52 exhibits a resistive force along an axis, which in the case of the illustrated embodiment is substantially parallel to the first axis 201 of the SELF web, when subjected to an applied elongation or axial elongation in a direction substantially parallel to the first axis 201. As used herein, the term "formed" refers to the creation of a desired structure or geometry upon a web material that will substantially retain the desired structure or geometry when it is not subjected to any externally applied elongations or forces. A SELF web of the present invention is comprised of at least a first region and a second region, wherein the first region is visually distinct from the second region. As used herein, the term "visually distinct" refers to features of the SELF web which are readily discernible to the normal naked eye when the SELF web or objects embodying the SELF web are subjected to normal use. A SELF web of the present invention is comprised of a strainable network of contiguous, "distinct", and "dissimilar" regions, wherein the strainable network includes at least a first region and a second region, where the first region has a "surface-pathlength" less than that of the second region, as measured parallel to a predetermined axis when the material is in an untensioned state. As used herein, the term "formed portion" refers to the portion of the material which is comprised of the desired structure or geometry of the strainable network. As used herein the term "surface-pathlength" refers to a measurement along the topographic surface of the region in question in a direction parallel to a predetermined axis. As used herein, the term "distinct" or "dissimilar" when referring to regions, refers to regions within the strainable network having measurably different surface-pathlengths as measured parallel to a predetermined axis while the SELF web is in an untensioned condition. The method for determining the surface-pathlength of the respective regions can be found in the Test Methods section set forth in subsequent portions of the present specification.

In the preferred embodiment shown in FIG. 2, the first regions 64 are substantially planar. That is, the material within the first region 64 is in substantially the same condition before and after the formation step undergone by the SELF web 52. The second regions 66 include a plurality of ribs or rib-like elements 74. The rib-like elements 74 may be embossed, debossed or a combination thereof.

The rib-like elements 74 have a first or major axis 76 which is substantially parallel to the second axis 200 of the SELF web 52, and a second or minor axis 77 which is substantially parallel to the first axis 201 of the SELF web 52. The first axis 76 of the rib-like elements 74 is at least equal to, and preferably longer than the second axis 77. Preferably, the ratio of the first axis 76 to the second axis 77 is at least about 1:1 or greater, and more preferably at least about 2:1 or greater.

The rib-like elements 74 within the second region 66 may be separated from one another by unformed areas. Preferably, the rib-like elements 74 are adjacent one another and are separated by an unformed area of less than 0.10 inches as measured perpendicular to the major axis 76 of the rib-like elements 74, and more preferably, the rib-like elements 74 are contiguous having no unformed areas between them.

The first region 64 and the second region 66 each have a "projected pathlength". As used herein the term "projected pathlength" refers to the length of a shadow of a region that would be thrown by parallel light. The projected pathlength of the first region 64 and the projected pathlength of the second region 66 are equal to one another. Accordingly, the overall dimension of the SELF web as measured parallel to the first axis 201 will be substantially the same before and after formation.

The second region 66 has a surface-pathlength, L2, greater than the surface-pathlength, L1, of the first region 64 as measured topographically in a direction parallel to the first axis of the SELF web while the SELF web is in an untensioned condition. Preferably, the surface-pathlength of the second region 66 is at least about 15% greater than that of the first region 64, more preferably at least about 30% greater than that of the first region, and most preferably at least about 70% greater than that of the first region. In general, the greater the surface-pathlength of the second region, the greater will be the elongation of the SELF web before encountering the force wall.

What makes the SELF web particularly well suited for use as the elastic zone 44 of the extensible back waist feature 43 is that it exhibits a modified "Poisson lateral contraction effect" substantially less than that of an otherwise identical base web of similar material composition. As used herein, the term "Poisson lateral contraction effect" describes the lateral contraction behavior of a material which is being subjected to an applied elongation. The method for determining the Poisson lateral contraction effect of a material can be found in the Test Methods section set forth in subsequent portions of the present specification. Preferably, the Poisson lateral contraction effect of the SELF web of the present invention is less than about 0.4 when the web is subjected to about 20% elongation. Preferably, the SELF web exhibits a Poisson lateral contraction effect less than about 0.4 when the web is subjected to about 40, 50 or even 60% elongation. More preferably, the Poisson lateral contraction effect is less than about 0.3 when the SELF web is subjected to 20, 40, 50 or 60% elongation. The Poisson lateral contraction effect of SELF webs of the present invention is determined by the amount of the web material which is occupied by the first and second regions, respectively. As the area of the SELF web material occupied by the first region increases, the Poisson lateral contraction effect also increases. Conversely, as the area of the SELF web material occupied by the second region increases the Poisson lateral contraction effect decreases. Preferably, the percent area of the SELF web material occupied by the first area is from about 2% to about 90%, and more preferably from about 5% to about 50%.

Web materials of the prior art which have at least one layer of an elastomeric material will generally have a large Poisson lateral contraction effect, i.e., they will "neck down" as they elongate in response to an applied force. SELF webs of the present invention can be designed to reduce if not substantially eliminate the Poisson lateral contraction effect of film based elastomeric webs of the prior art.

For SELF web material 52, the direction of applied axial elongation, D, indicated by arrows 80 in FIG. 2, is substantially perpendicular to the first axis 76 of the rib-like elements 74. As the rib-like elements 74 are able to unbend or geometrically deform in a direction substantially perpendicular to their first axis 76, the direction of applied elongation to cause extension in the SELF web 52 is also substantially perpendicular to the first axis 76 of the rib-like elements 74.

Figure 3:
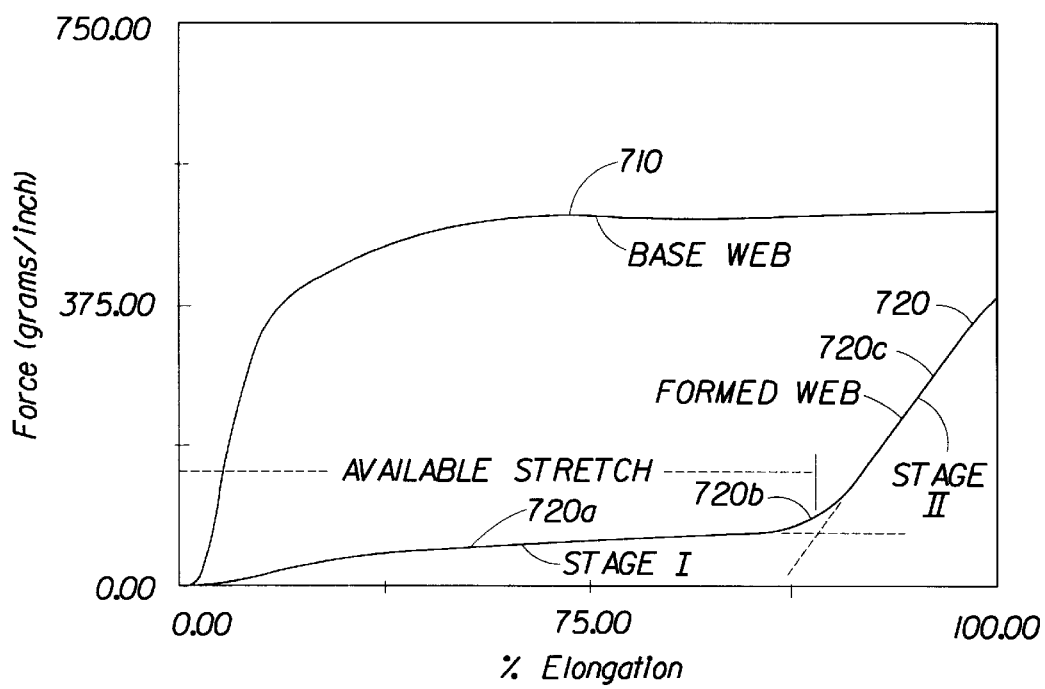
FIG. 3 is a graph of the resistive force versus percent elongation comparing the behavior of a SELF web of the present invention, as shown in FIG. 5, formed from Clopay 1401, with a base web of similar material composition.

In FIG. 3 there is shown a graph of the resistive force-elongation curve 720 of a formed polymeric SELF web material along with a curve 710 for a base film of similar composition. Specifically the samples are polymeric web materials, comprised substantially of linear low density polyethylene, approximately 0.001" thick, designated sample 1401 available from Clopay, Cincinnati Ohio. The method for generating the resistive force-elongation curves can be found in the Test Methods section set forth in subsequent portions of the present specification. Referring now to the force-elongation curve 720, there is an initial substantially linear, lower force versus elongation stage I designated 720a, a transition zone designated 720b which indicates the encounter of the force wall, and a substantially linear stage II designated 720c which displays substantially higher force versus elongation behavior.

As seen in FIG. 3 the SELF web exhibits different elongation behavior in the two stages when subjected to an applied elongation in a direction parallel to the first axis of the SELF web. The resistive force to the applied elongation is significantly different between stage I (720a) and stage II (720c) of cure 720 as compared to curve 710 which does not exhibit this behavior. As seen in FIG. 3, the SELF web exhibits different elongation behavior in the two stages when subjected to an applied elongation in a direction parallel to the first axis of the SELF web. The resistive force exerted by the SELF web to the applied elongation is significantly less in the stage I region (720a) versus the stage II region (720c) of curve 720. Furthermore, the resistive force exerted by the SELF web to the applied elongation as depicted in stage I (720a) of curve 720 is significantly less than the resistive force exerted by the base web as depicted in curve 710 within the limits of elongation of stage I. As the SELF web is subjected to further applied elongation and enters stage II (720c) the resistive force exerted by the SELF web increases and approaches the resistive force exerted by the base web. The resistive force to the applied elongation for the stage I region (720a) of the SELF web is provided by the molecular-level deformation of the first region of the SELF web and the geometric deformation of the second region of the SELF web. This is in contrast to the resistive force to an applied elongation that is provided by the base web, depicted in curve 710, which results from molecular-level deformation of the entire web. SELF web materials can be designed to yield virtually any resistive force in stage I which is less than that of the base web material by adjusting the percentage of the web surface which is comprised of the first and second regions, respectively. The force-elongation behavior of stage I can be controlled by adjusting the width, cross-sectional area, and spacing of the first region and the composition of the base web.

Figure 4A:
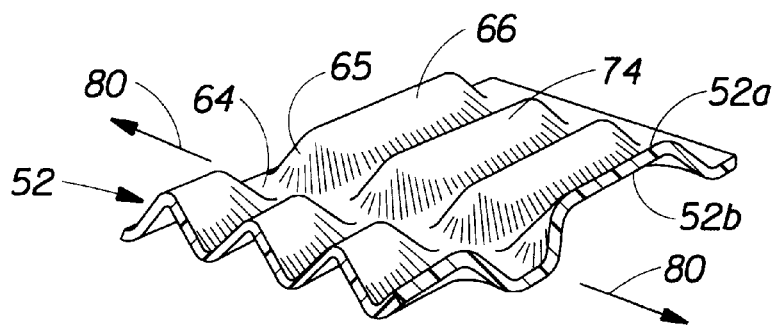
FIG. 4A is a segmented, perspective illustration of a SELF web in an untensioned condition.
Figure 4B:
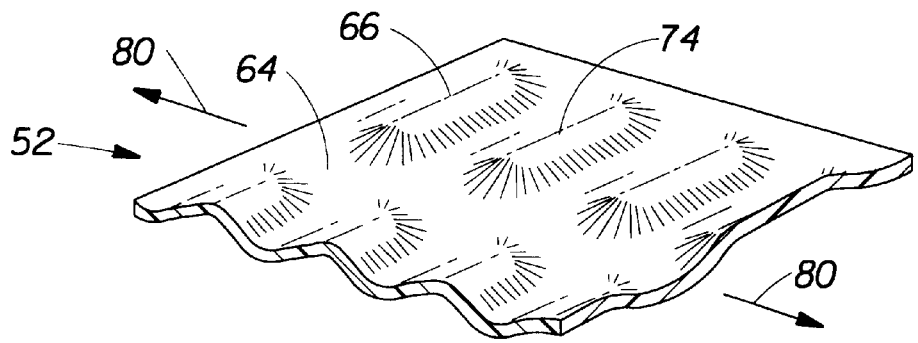
FIG. 4B is a segmented, perspective illustration of a SELF web in a tensioned condition corresponding to stage I on the force-elongation curve depicted in FIG. 3.
Figure 4C:
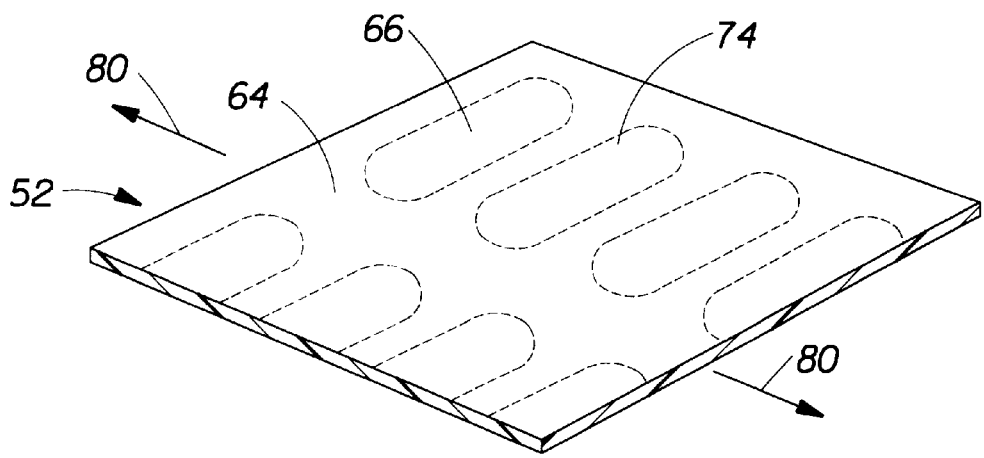
FIG. 4C is a segmented perspective illustration of a SELF web in a tensioned condition corresponding to stage II on the force-elongation curve depicted in FIG. 3.

Referring now to FIGS. 4A–4C, as SELF web 52 is subjected to an applied axial elongation, D, indicated by arrows 80, the first region 64 having the shorter surface-pathlength, L1, provides most of the initial resistive force, P1, as a result of molecular-level deformation, to the applied elongation which corresponds to stage I. While in stage I, the rib-like elements 74 in the second region 66 are experiencing geometric deformation, or unbending and offer minimal resistance to the applied elongation. In the transition zone (720b) between stages I and II, the rib-like elements 74 are becoming aligned with the applied elongation. That is, the second region is exhibiting a change from geometric deformation to molecular-level deformation. This is the onset of the force wall. In stage II, as seen in FIG. 4C, the rib-like elements 74 in the second region 66 have become substantially aligned with the plane of applied elongation (i.e. the second region has reached its limit of geometric deformation) and begin to resist further elongation via molecular-level deformation. The second region 66 now contributes, as a result of molecular-level deformation, a second resistive force, P2, to further applied elongation. The resistive forces to elongation depicted in stage II by both the molecular-level deformation of the first region 64 and the molecular-level deformation of the second region 66 provide a total resistive force, PT, which is greater than the resistive force depicted in stage I which is provided by the molecular-level deformation of the first region 64 and the geometric deformation of the second region 66. Accordingly, the slope of the force-elongation curve in stage II is significantly greater than the slope of the force-elongation curve in stage I.

The resistive force P1 is substantially greater than the resistive force P2 when (L1+D) is less than L2. When (L1+D) is less than L2 the first region provides the initial resistive force P1, generally satisfying the equation:

$$P1 = \frac{(A1 \times E1 \times D)}{L1}$$

When (L1+D) is greater than L2 the first and second regions provide a combined total resistive force PT to the applied elongation, D, generally satisfying the equation:

$$PT = \frac{(A1 \times E1 \times D)}{L1} + \frac{(A2 \times E2 \times |L1 + D - L2|)}{L2}$$

The maximum elongation occurring while in stage I is the "available stretch" of the SELF web. The available stretch corresponds to the distance over which the second region experiences geometric deformation. The available stretch can be effectively determined by inspection of the force-elongation curve 720 as shown in FIG. 3. The approximate point at which there is an inflection in the transition zone between stage I and stage II is the percent elongation point of "available stretch". The range of available stretch can be varied from about 10% to 100% or more; this range of elongation is often found to be of interest in disposable absorbent articles, and can be largely controlled by the extent to which the surface-pathlength L2 in the second region exceeds the surface-pathlength L1 in the first region and the properties (composition) of the base film. The term available stretch is not intended to imply a limit to the elongation which the SELF web may be subjected to as there are applications where elongation beyond the available stretch is desirable. Significantly higher forces are required to achieve percent elongations in the base film equivalent to those percent elongations in the SELF web. The approximate extent of stage I can be controlled as desired by adjusting the pathlengths, L1 and L2, in an untensioned condition. The force-elongation behavior of stage I can be controlled by adjusting the width, thickness, and spacing of first region 64 and the properties of the base film.

Figure 5:
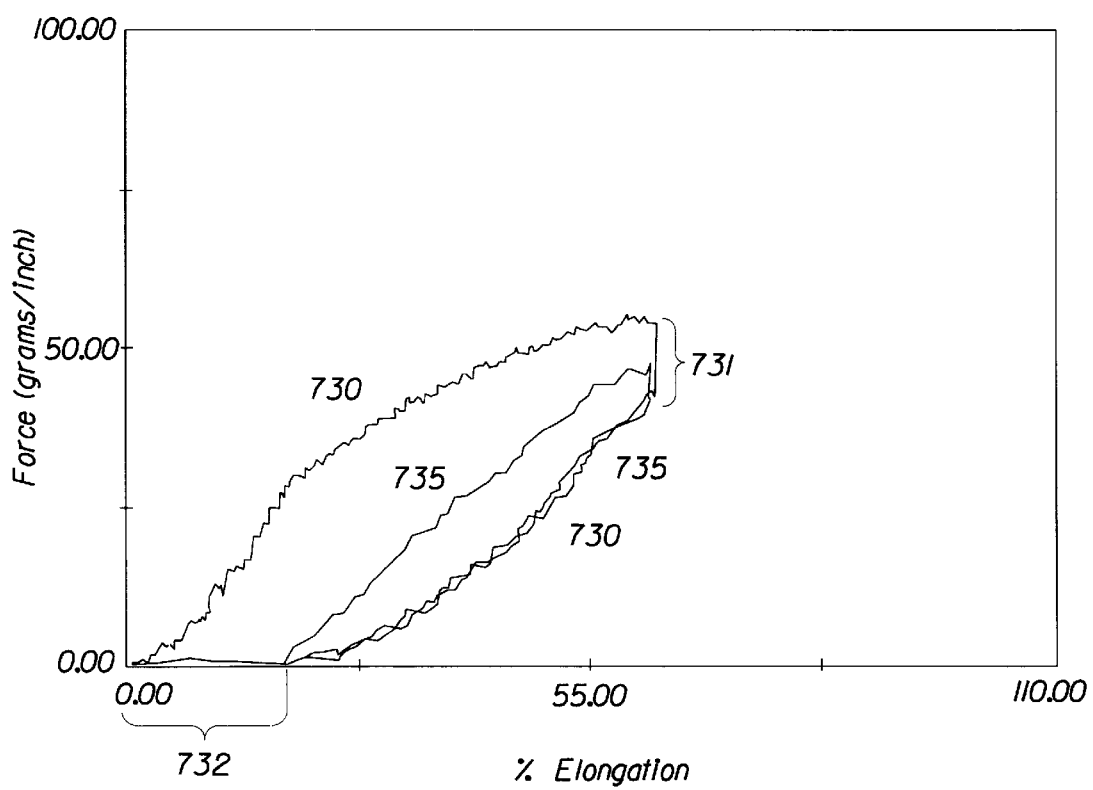
FIG. 5 is a graph of the elastic hysteresis behavior of the SELF web which is graphically represented by curve 720 in FIG. 3 when the SELF web is subjected to a hysteresis test at 60% elongation.

The curves 730 and 735 in FIG. 5 depict the elastic hysteresis behavior exhibited by the SELF web. The sample is the same as used to produce the graph in FIG. 3 (Clopay 1401). The sample was examined for elastic hysteresis behavior at an elongation of 60%. Curve 730 represents the response to an applied and released elongation during the first cycle and curve 735 represent the response to an applied and released elongation during the second cycle. The force relaxation during the first cycle 731 and the percent set 732 are depicted in FIG. 5. Note that significant recoverable elongation, or useful elasticity, is exhibited at relatively low forces over multiple cycles, i.e., this means the SELF web can easily expand and contract to a considerable degree. The method for generating the elastic hysteresis behavior can be found in the Test Method section set forth in subsequent portion of the present specification.

When the SELF web is subjected to an applied elongation, the SELF web exhibits an elastic-like behavior as it extends in the direction of applied elongation and returns to its substantially untensioned condition once the applied elongation or force is removed, unless extended beyond the point of yielding. The SELF web is able to undergo multiple cycles of applied elongation without losing its ability to substantially recover. Accordingly, the SELF web is able to return to its substantially untensioned condition once the applied elongation is removed.

While the SELF web may be easily and reversibly extended in the direction of applied axial elongation, in a direction substantially perpendicular to the first axis 76 of the rib-like elements, the SELF web is not as easily extended in a direction substantially parallel to the first axis of the rib-like elements. The formation of the rib-like elements allows the rib-like elements to geometrically deform in a direction substantially perpendicular to the first or major axis of the rib-like elements, while requiring substantially molecular-level deformation to extend in a direction substantially parallel to the first axis of the rib-like elements.

The amount of applied force required to extend the SELF web is dependent upon the composition and thickness of the base material forming the SELF web and the width and spacing of the first regions, with narrower and more widely spaced first regions requiring lower applied extensional forces to achieve the desired elongation for a given composition and thickness. The first axis 68, (i.e., the length) of the undeformed first regions is preferably greater than the second axis 69, (i.e., the width) with a preferred length to width ratio of about 5:1 or greater.

The depth and number of rib-like elements 74 can also be varied to control the extension force and available stretch of the SELF web. The available stretch or elongation is increased if for a given number of rib-like elements, the height or degree of formation imparted on the rib-like elements is increased. Similarly, the available stretch is increased if for a given height or degree of formation, the number or frequency of the rib-like elements is increased.

There are several functional properties that can be controlled through the application of the present invention. There is the resistive force exerted by the SELF web against an applied elongation and the available stretch of the SELF web before the force wall is encountered. The resistive force that is exerted by the SELF web against an applied elongation is a function of the material (e.g., composition, molecular structure and orientation, etc.) and thickness and the percent of the projected surface area of the SELF web that is occupied by the first region. The higher the percent area coverage of the SELF web by the first region, the higher the resistive force that the SELF web will exert against an applied elongation for a given material composition and thickness. The percent coverage of the SELF web by the first region is determined in part if not wholly by the width of the first region and the spacing between adjacent first regions.

The available stretch of the SELF web is determined by the surface-pathlength of the second region. This is determined at least in part by the rib-like elements spacing, rib-like element frequency and depth of formation of the rib-like elements as measured perpendicular to the plane of the SELF web. In general, the greater the surface-pathlength of the second region the greater the available stretch of the SELF web.

While an entire SELF web may include a strainable network of first and second regions, the present invention may also be practiced by providing only specific portions of the SELF web with a strainable network comprised of first and second regions.

The configuration and spacing of the first and second regions may also be varied to vary the characteristics of the SELF web. For example, the second regions may comprise curvilinear rib-like elements, or the first regions and the second regions may be curvilinear. The SELF web may also exhibit an elastic-like behavior along a plurality of axes by extending the axes in a radial, fan-like array to allow the SELF web to exhibit an elastic-like behavior along a plurality of axes. For example, the multiple axes may be positioned at various angles to one another such as 45°, 90°, 135°, etc. In addition to the various angles of orientation, the regions themselves may be straight, curvilinear, or combinations thereof The surface-pathlengths in the second region may also provide a difference in amplitude of the rib-like elements such that the SELF web will have different zones of available stretch. It is also possible that the rib-like elements can be varied between adjacent regions to provide different available stretches in the adjacent second regions. The widths of the first region may also vary across the web with the narrower regions offering a lower resistive force to an applied elongation as compared to the higher resistive force offered by the wider first region.

The SELF web also need not be extensible only in the direction parallel to the lateral centerline 101 of the diaper 30 as shown in FIG. 1. For example, the first axis and the second axis of the SELF web may be disposed at an angle to the longitudinal centerline and lateral centerline of the diaper 30, respectively. Thus, the SELF web would axially elongate along a line at an angle to the lateral centerline of the diaper. This angle is preferably between about 0° and about 30° for the diapers of the present invention. Further, portions of the SELF web may have different angles of extensibility.

Referring to FIG. 2, the expansive zone 45, and the elastic-like zone 44 meet at a common border 120. In the embodiment shown in FIG. 2, the border 120 is substantially parallel to the axis of expansion and contraction, axis 201. The expansive zone 45 includes a plurality of incrementally stretched regions 110. The incrementally stretched regions 110 are formed by subjecting the expansive zone 45 to mechanical stretching such as an incremental stretching system as will be described in greater detail hereinafter.

The incrementally stretched regions 110 have been stretched, strained, or elongated in a direction parallel to the first axis 201 of the SELF web 52. The incremental stretching of regions 110 of expansive zone 45 allow the expansive zone to effectively elongate (yield) when the elastic-like zone 44 is extended, without generating any excessive tensional forces. The expansive zone 45 has a surface-pathlength greater than the surface-pathlength of the first region 64 of the SELF web 52 of the elastic-like zone 44 as measured in a direction parallel to the first axis 201 of the SELF web 52 while both zones are in an untensioned condition. In addition, the expansive zone 45 has a surface-pathlength different than the surface-pathlength of the second region 66 of the SELF web 52 of the elastic-like zone 44 as measured in a direction parallel to the first axis 201 of the SELF web 52 while both zones are in an untensioned condition.

As the extensible waist feature 43 is subjected to an applied axial elongation indicated by arrows 80, the expansive zone 45 provides a relatively low resistive force to the applied elongation as the expansive zone 45 undergoes substantially geometric deformation. The incrementally stretched regions 110 initially experience geometric deformation or unbending and offer minimal resistance to the applied elongation. As elongation continues the incrementally stretched regions 110 become substantially aligned with the plane of elongation (the incrementally stretched regions 110 have reached their limit of geometric deformation) and they begin to resist further elongation via molecular-level deformation. The expansive zone 45 now contributes a higher resistive force as a result of this molecular-level deformation. The amount or extent of geometric deformation that the expansive zone will undergo before experiencing molecular-level deformation is dependent at least to some degree upon the amount of pre-straining or stretching that is imparted upon the expansive zone.

If the expansive zone 45 has a surface-pathlength greater than the surface-pathlength of the second region 66, the second region 66 will first begin to contribute a significant resistive force before the expansive zone 45 contributes a significant resistive force. Alternatively, if the expansive zone 45 has a surface-pathlength less than the surface-pathlength of the second region 66, the expansive zone 45 will be the first to contribute a significant resistive force.

Preferably, the expansive zone 45 must be free of restrictions to expansion for a certain distance from the elastic-like zone 44 which distance is indicated as 121 in FIG. 2, to permit the elastic-like zone 44 to elastically expand and contract within its designed limits. Examples of restrictions to expansion are bonding the expansive zone 45 to a non-expansive member such as an absorbent core, a tape fastening member, or a topsheet. It should be recognized by those skilled in the art that distance 121 will depend on the desired amount of elastic expansion and contraction in elastic-like zone 44, the surface-pathlength of expansive zone 45 and the nature of the potential restriction of movement.

Figure 6:
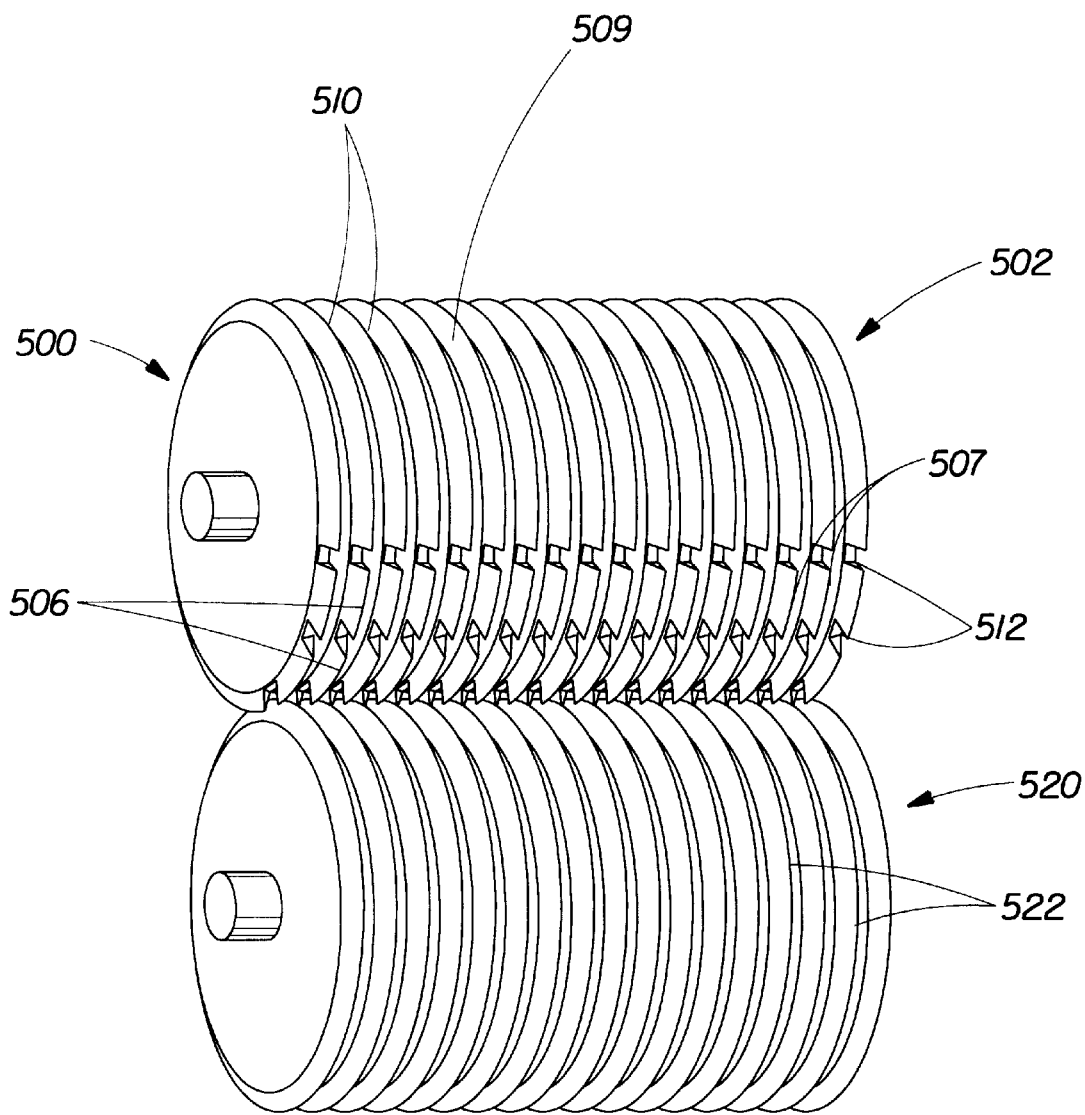
FIG. 6 is a simplified illustration of a preferred apparatus used to form the extensible waist belt of FIG. 2.

Referring now to FIG. 6, there is shown an apparatus generally indicated as 500 for forming the extensible back waist feature 43 comprising both the elastic-like zone 44 and the expansive zone 45, where the elastic-like zone 44 comprises a SELF web and the expansive zone comprises a prestrained web comprising incrementally stretched regions. Apparatus 500 employs opposed pressure applicators having three-dimensional surfaces which at least to a degree are complimentary to one another. Apparatus 500 comprises a pair of intermeshing rolls 502 and 520. Roll 502 includes a plurality of first corrugated or toothed regions 506, a plurality of second corrugated or toothed regions 509, and a plurality of grooved regions 512. Grooved regions 512 extend in a direction substantially parallel to a longitudinal axis running through the center of cylindrical roll 502. In the embodiment shown in FIG. 6, roll 502 includes three grooved regions 512. However, roll 502 may include any number of grooved regions 512. Toothed region 506 which are located between grooved regions 512, include a plurality of teeth 507. Toothed regions 509 include a plurality of teeth 510. Roll 520 includes a plurality of teeth 522 which mesh with teeth 507 and 510 of roll 502.

As a web, such as a backsheet 33 of disposable diaper 30, is directed through apparatus 500 between intermeshing rolls 502 and 520, the portion of the web passing between toothed regions 509 containing teeth 510, and teeth 522 on roll 520 will be incrementally stretched forming incrementally stretched regions which correspond to incrementally stretched regions 110 in the expansive zone 45, shown in FIG. 2. The portion of the web passing between grooved regions 512 and teeth 522 on roll 520 will remain unformed, thus providing unformed regions in the web which correspond to the first regions 64 of the SELF web 52 shown in FIG. 2. The portions of the web passing between toothed regions 506 containing teeth 507 and teeth 522 on roll 520 will be incrementally stretched forming rib-like elements in the web which correspond to rib-like elements 74 in the second regions 66 of the SELF web 52 shown in FIG. 2.

The exact configuration, spacing and depth of the teeth on the rolls 502 and 520 may be varied depending on the amount of incremental stretching desired. The degree of overlap of the teeth on rolls 502 and 520 may also be adjusted, as desired, to produce more or less incremental stretching.

While the extensible waist feature comprising the elastic-like zone and the expansive zone has been described as a single layer of polymeric material, the present invention may be practiced equally well with other materials or with laminates of two or more materials. Examples of suitable materials include two-dimensional apertured films, macroscopically expanded, three-dimensional, apertured formed films. Examples of other suitable materials include composite structures or laminates of polymer films, and nonwovens. Laminates of polymer films and nonwovens may also comprise absorbent or fibrous absorbent materials, foams, or other compositions. Examples of such laminates include a nonwoven topsheet and a polymeric film backsheet found on commercially available disposable diapers. Additional reinforcing elements can also be added for strength and recovery benefits.

The expansive zone and the elastic-like zone may also be used on other portions of the diaper. For example, the expansive zone and the elastic-like zone may be used to form the elasticized leg cuffs 35, the front waist feature 90, or the ear flaps 92. In addition, the expansive zone and the elastic-like zone may be used to form other extensible portions on the diaper.

The present invention is intended to produce a functional equivalent to a conventional diaper having an elastic member secured to diapers to provide contractive and expansive properties. Conventional diapers are made by bonding an elastic member in a tensioned state to the topsheet and backsheet in the waist area. After bonding, the tension is released causing gathers to form in the waist. By use of the elastic-like and expansive zones of the present invention, the same result is accomplished without the addition of an elastic member.

Figure 7:
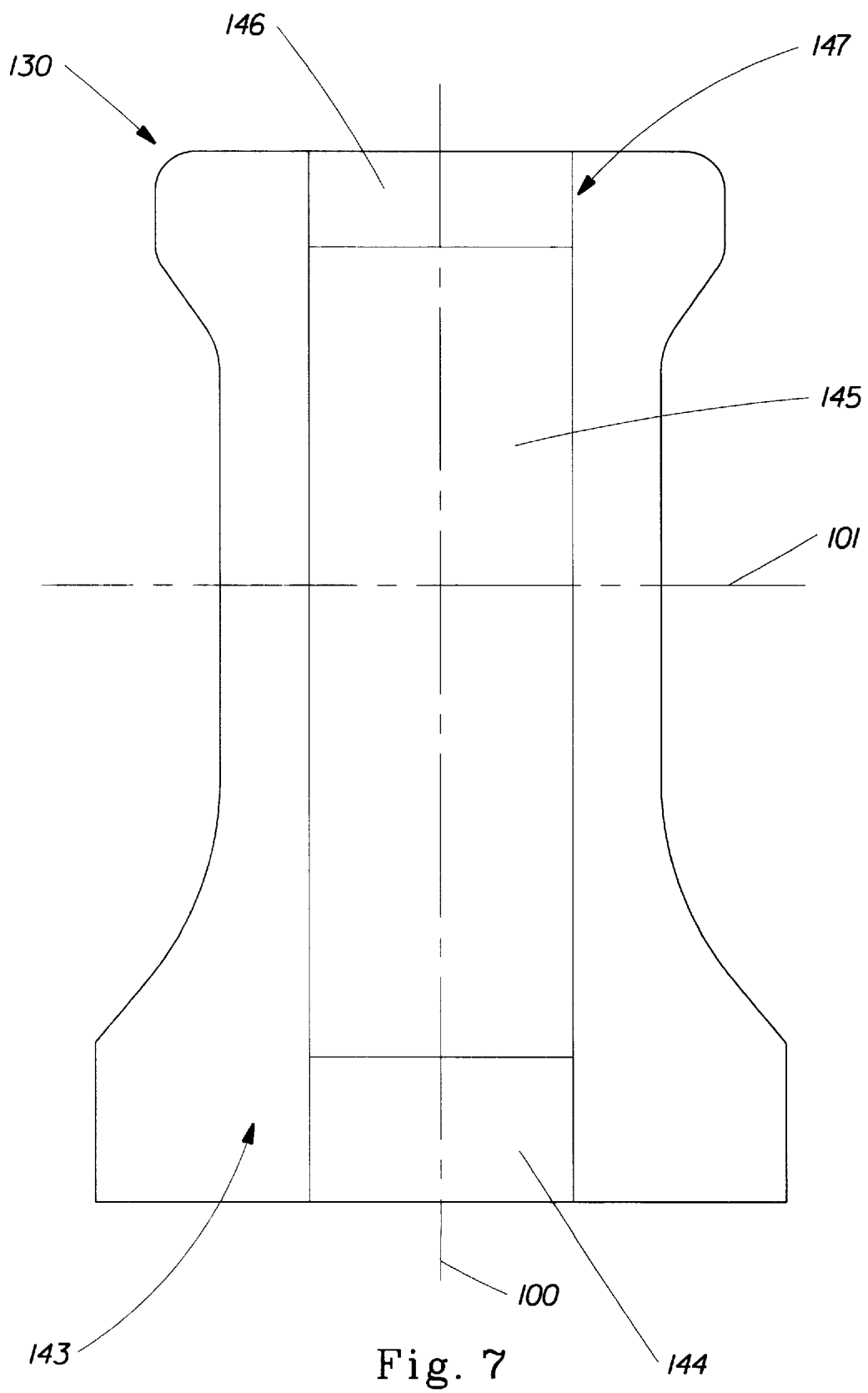
FIG. 7 is a plan view of another embodiment of a diaper of the present invention.

Referring now to FIG. 7 there is shown a plan view of another embodiment of a diaper 130 of the present invention. Diaper 130 comprises a backsheet 133 comprising an extensible back waist feature 143 and an extensible front waist feature 147, a topsheet and a backsheet, (for simplification the topsheet and backsheet are not shown in FIG. 7). Back waist feature 143 comprises an elastic-like zone 144 and an expansive zone 145. Front waist feature 147 comprises an elastic-like zone 146 and an expansive zone 145. In this embodiment the axis of elastic contraction and expansion in the elastic-like zones and the direction of expansion in the expansive zone are parallel to each other and also to the transverse axis 101.

The expansive zone 145 will cover part, or preferably, all of the width and length of the underlying absorbent core of the diaper which is added in a later step in the assembly. The width, length and amount of expansion of the expansive zone 145 can be adjusted to provide the desired properties. The unexpanded width of the expansion zone 145, (as measured in a direction parallel to the transverse axis 101), can be larger, smaller, or the same as the unexpanded width of the elastic-like zones 144 and 146. However, only the portion of elastic-like zone which has a common boundary with the expansive zone will behave contractively in the finished product to produce a gathered waist feature. The unexpanded width of the expansive zone 145 is shown in FIG. 7 as being equal to the unexpanded width of the elastic-like zones 144 and 146 which maximizes the amount the elastic-like zones contract relative to the expansive zone 145.

The surface-pathlength of the expansive zone 145 determines the amount of relative "contraction" of the elastic-like zones. For example, if the surface-pathlength of the expansive zone is 40% longer than the elastic-like zone, the elastic-like zone has the potential to exhibit 40% contracted stretch in the finished product.

Figure 8:
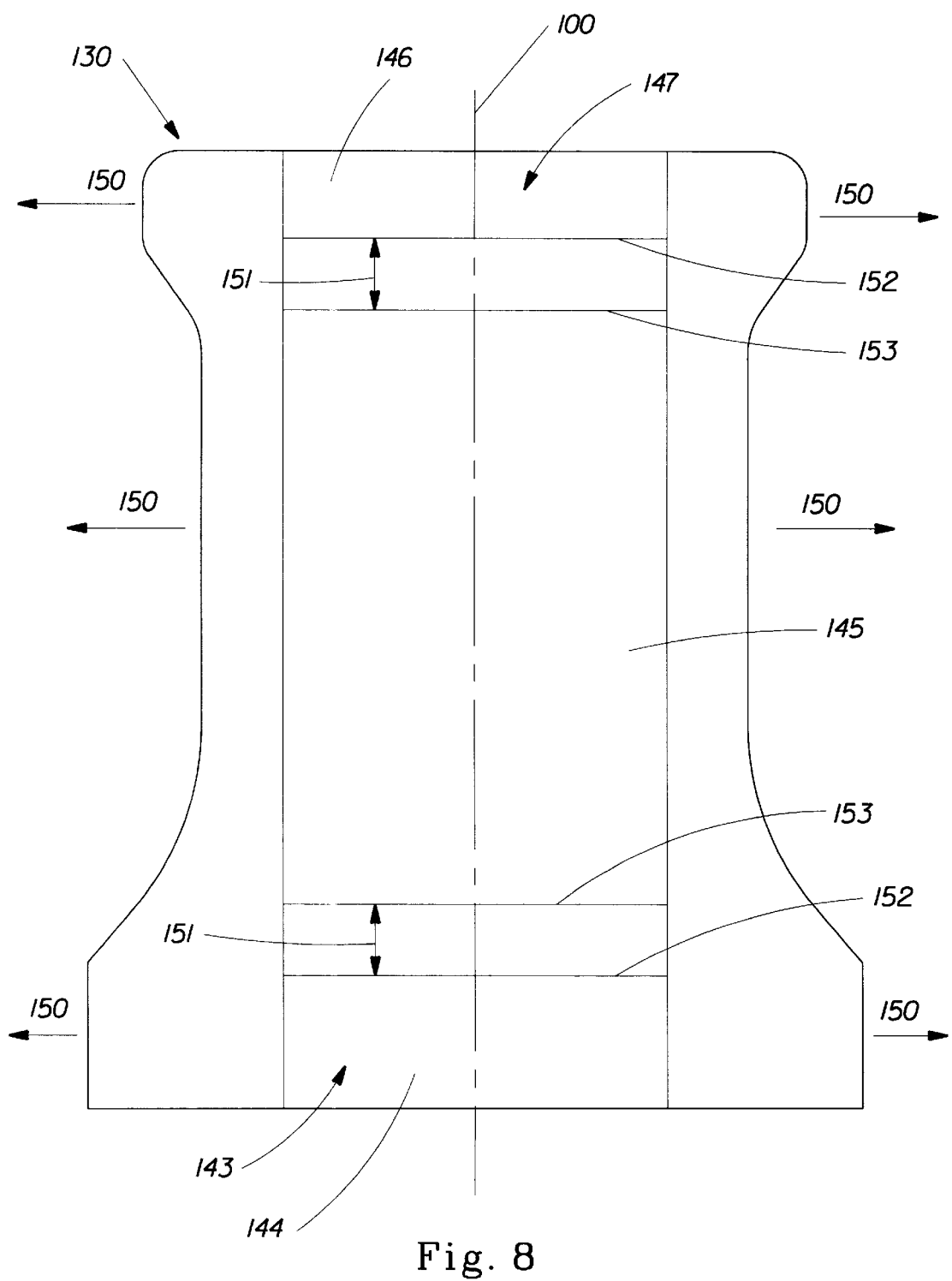
FIG. 8 is a plan view of the diaper of FIG. 7 in a tensioned or stretched condition.

In FIG. 8 the diaper 130 is stretched in the direction indicated by arrows 150 to fully extend the expansive zone 145 and to put the elastic-like zones 144 and 146 under tension. Similar to distance 121 in FIG. 2, distance 151 between lines 152 and 153 of FIG. 8, represents the minimal distances the expansive zone must extend uninhibited, e.g., unbonded to another layer such as an absorbent core, from the elastic-like zone to produce the elastically expansive and contractive behavior. Line 152 represents the common border between the two zones. Line 153 can represent the waist edge of the absorbent core or it can represent the topmost extent of the bond between the core and the backsheet. The distance 151 must be determined so that the elastic-like zone can contract without hindrance to its unstrained length when the tension is removed.

Although FIG. 8 indicates a single uniform expansive zone having the same width as the elastic-like zones, it should be understood that as long as the requirement for unhindered motion is met between lines 152 and 153, the remainder of the expansive zone could have multiple regions with different widths and surface-pathlengths.

Figure 9:
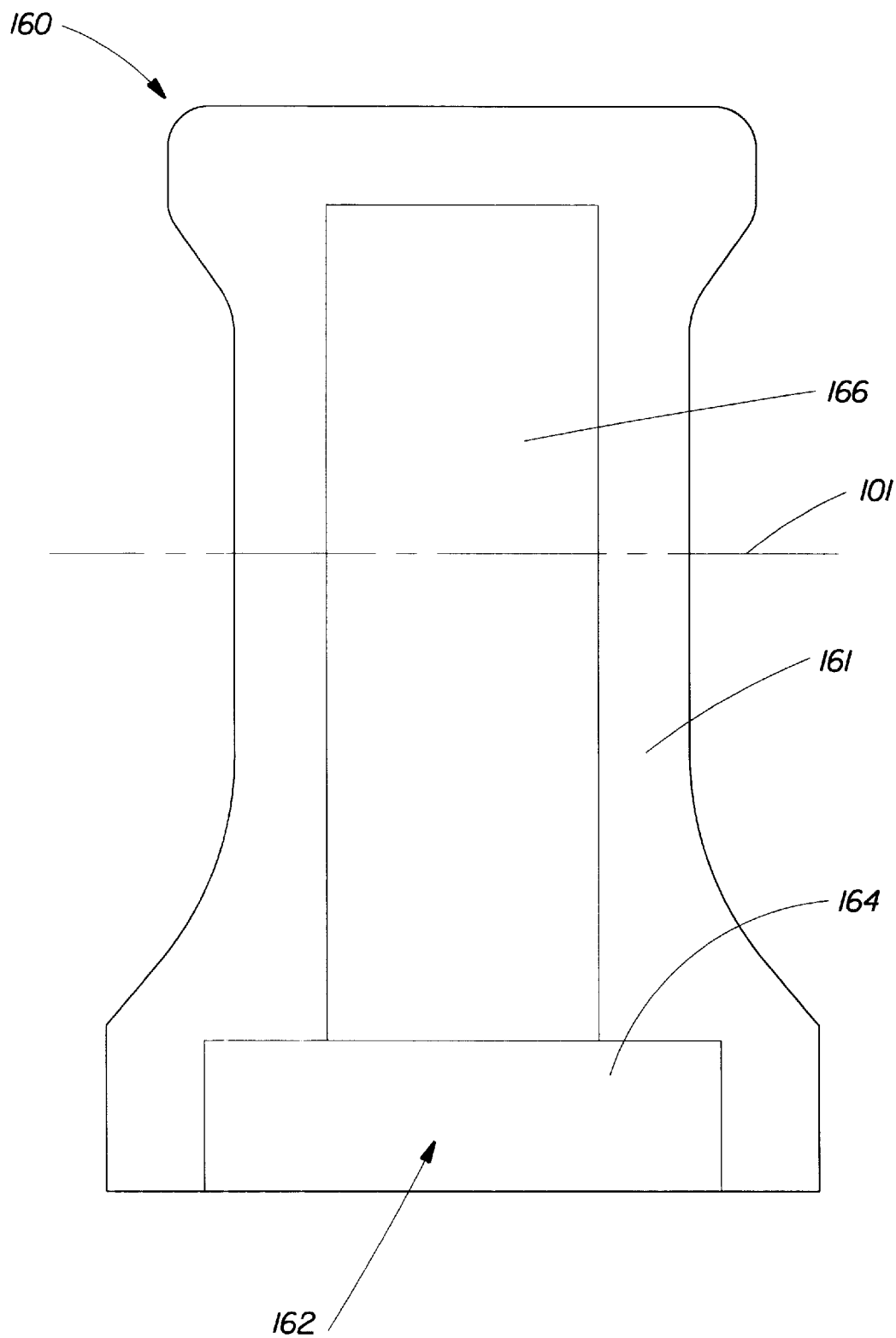
FIG. 9 is a plan view of another embodiment of a diaper of the present invention.

Referring now to FIG. 9, there is shown a plan view of another embodiment of a diaper 160 of the present invention. Diaper 160 comprises a backsheet 161 comprising an extensible back waist feature 162 comprising an elastic-like zone 164 and an expansive zone 166. The width of the expansive zone 164, (as measured in a direction parallel to the transverse centerline 101), is greater than the width of the adjacent expansive zone 166. The expansive zone 166 may extend to the longitudinal edge of the diaper.

To make a diaper of the present invention, the backsheet is first provided with the desired arrangement of elastic-like and expansive zones. The backsheet is then tentered or extended to expand the expansive zone. An absorbent core is then bonded to the expansive zone while the expansive zone is in its expanded condition by any suitable means, for example, thin spirals of glue. A suitable topsheet is then bonded to the absorbent core and backsheet. The topsheet is sized substantially the same as the backsheet. Once the tension is removed, the elastic-like zones will contract causing the elastic-like zones to neck down and gather.

Alternatively, the diaper may be made by first providing the backsheet with one or more expansive zones. The expansive zones are then expanded and secured to another substrate such as an absorbent core. A topsheet is then secured to the backsheet and absorbent core. The elastic-like zones are then formed in both the topsheet and the backsheet.

Other suitable methods may also be used to manufacture the diaper of the present invention. In addition, the order of steps may be also be changed. Furthermore, some steps may also be combined with other steps.

Referring again to FIG. 8, the bonding of the backsheet to the absorbent core becomes very important. The absorbent core may have any length, for example, the absorbent core may extend substantially along the entire length of the diaper. However, line 153 in FIG. 8, represents the uppermost limit of bonding between the core and the backsheet. As seen in FIG. 8, line 153 is completely within expansive zone 145. If line 153 is located within the elastic-like zone, it will significantly inhibit the contractive and expansive properties of the elastic-like zone, thus significantly eliminating the benefits of the expansive zone, i.e., the removal of the line of tension. It should be noted that a portion of the elastic-like zone may be bonded to the absorbent core to keep the absorbent core from floating. Preferably, such bonding will be at or near centerline 100 where the amount of expansion and contraction of the elastic-like zone is at a minimum.

Test Methods

Surface-Pathlength

Pathlength measurements of formed material regions are to be determined by selecting and preparing representative samples of each distinct region and analyzing these samples by means of microscopic image analysis methods.

Samples are to be selected so as to be representative of each region's surface geometry. Generally, the transition regions should be avoided since they would normally contain features of both the first and second regions. The sample to be measured is cut and separated from the region of interest. The "measured edge" is to be cut parallel to a specified axis of elongation. Usually this axis is parallel to the formed primary-axis of either the first region or the second region. An unstrained sample length of one-half inch is to be "gauge marked" perpendicular to the "measured edge": while attached to the web material, and then accurately cut and removed from the web material.

Measurement samples are then mounted onto the long-edge of a microscopic glass slide. The "measured edge" is to extend slightly (approximately 1 mm) outward from the slide edge. A thin layer of pressure-sensitive adhesive is applied to the glass face-edge to provide a suitable sample support means. For highly formed sample regions it has been found desirable to gently extend the sample in its axial direction (without imposing significant force) simultaneous to facilitate contact and attachment of the sample to the slide-edge. This allows improved edge identification during image analysis and avoids possible "crumpled" edge portions that require additional interpretation analysis.

Images of each sample are to be obtained as "measured edge" views taken with the support slide "edge on" using suitable microscopic measuring means of sufficient quality and magnification. FIG. 38 shows a typical view of a portion of the second region of a sample 900 having a first side edge 901 and a second side edge 902 used to determine the surface-pathlength. Data herein presented was obtained using the following equipment; Keyence VH-6100 (20× Lens) video unit, with video-image prints made with a Sony Video printer Mavigraph unit. Video prints were image-scanned with a Hewlett Packard ScanJet IIP scanner. Image analysis was on a MacIntosh IICi computer utilizing the software NIH MAC Image version 1.45.

Using this equipment, a calibration image initially taken of a grid scale length of 0.500" with 0.005" increment-marks to be used for calibration setting of the computer image analysis program. All samples to be measured are then video-imaged and videoimage printed. Next, all video-prints are image-scanned at 100 dpi (256-level gray scale) into a suitable Mac image-file format. Finally, each image-file (including calibration file) is analyzed utilizing Mac Image 1.45 computer program. All samples are measured with freehand line-measurement tool selected. Samples are measured on both side-edges and the lengths are recorded. Simple film-like (thin & constant thickness) samples require only one side-edge to be measured. Laminate and thick foam samples are measured on both side-edges. Length measurement tracings are to be made along the full gauge length of a cut sample. In cases of highly deformed samples, multiple (partially overlapping) images may be required to cover the entire cut sample. In these cases, select characteristic features common to both overlapping-images and utilize as "markers" to permit image length readings to adjoin but not overlap.

The final determination of surface-pathlength for each region is obtained by averaging the lengths of five (5) separate ½" gauge-samples of each region. Each gauge-sample "surface-pathlength" is to be the average of both side-edge surface-pathlengths.

While the test method described above is useful for many of the web materials of the present invention it is recognized that the test method may have to be modified to accommodate some of the more complex web materials within the scope of the present invention.

Poisson's Lateral Contraction Effect

The Poisson's lateral contraction effect is measured on an Instron Model 1122, as available from Instron Corporation of Canton, Mass., which is interfaced to a Gateway 2000 486/33 Hz computer available from Gateway 2000 of N. Sioux City, S.D., using Test Works™ software which is available from Sintech, Inc. of Research Triangle Park, N.C. All essential parameters needed for testing are input in the TestWorks™ software for each test. Data collection is accomplished through a combination of manual sample width measurements, and elongation measurements made within TestWorks™.

The samples used for this test are 1" wide×4" long with the long axis of the sample cut parallel to the direction of the first region of the sample. The sample should be cut with a sharp knife or suitably sharp cutting device designed to cut a precise 1" wide sample. It is important that a "representative sample" should be cut so that an area representative of the symmetry of the overall pattern of the deformed region is represented. There will be cases (due to variations in either the size of the deformed portion or the relative geometries of regions 1 and 2) in which it will be necessary to cut either larger or smaller samples than is suggested herein. In this case, it is very important to note (along with any data reported) the size of the sample, which area of the deformed region it was taken from and preferably include a schematic of the representative area used for the sample. In general, an "aspect ratio" of (2:1) for the actual extended tensile portion (L1:w1) is to be maintained if possible. Five samples are tested.

The grips of the Instron consist of air actuated grips designed to concentrate the entire gripping force along a single line perpendicular to the direction of testing elongation having one flat surface and an opposing face from which protrudes a half round. No slippage should be permitted between the sample and the grips. The distance between the lines of gripping force should be 2" as measured by a steel rule held beside the grips. This distance will be referred to from here on as the "gauge length".

The sample is mounted in the grips with its long axis perpendicular to the direction of applied elongation. An area representative of the overall pattern geometry should be symmetrically centered between the grips. The crosshead speed is set to 10 in/min. The crosshead moves to the specified strain (measurements are made at both 20 and 60% elongation). The width of the sample at its narrowest point (w2) is measured to the nearest 0.02" using a steel rule. The elongation in the direction of applied extension is recorded to the nearest 0.02" on the TestWorks software. The Poisson's Lateral Contraction Effect (PLCE) is calculated using the following formula:

$$PLCE = \frac{\frac{|w2 - w1|}{w1}}{\frac{|l2 - l1|}{l1}}$$

where
- w2=The width of the sample under an applied longitudinal elongation;
- w1=The original width of the sample;
- L2=The length of the sample under an applied longitudinal elongation; and
- L1=The original length of the sample (gauge length);

Measurements are made at both 20 and 60% elongation using five different samples for each given elongation. The PLCE at a given percent elongation is the average of five measurements.

While the test method described above is useful for many of the web materials of the present invention it is recognized that the test method may have to be modified to acconmmodate some of the more complex web materials within the scope of the present invention.

Hysteresis Test

The hysteresis test is used for measuring the percent set and percent force relaxation of a material. The tests are performed on an Instron Model 1122, available from Instron Corporation of Canton, Mass. which is interfaced to a Gateway 2000 486/33 Hz computer available from Gateway 2000 of N. Sioux City, S.D. 57049, using TestWorks™ software which is available from Sintech, Inc. of Research Triangle Park, N.C. 27709. All essential parameters needed for testing are input in the TestWorks™ software for each test (i.e. Crosshead Speed, Maximum percent elongation Point and Hold Times). Also, all data collection, data analysis and graphing are done using the TestWork™ software.

The samples used for this test are 1" wide×4" long with the long axis of the sample cut parallel to the direction of maximum extensibility of the sample. The sample should be cut with a sharp exacto knife or some suitably sharp cutting device design to cut a precise 1" wide sample. (If there is more than one direction of elongation of the material, samples should be taken parallel to representative directions of elongation). The sample should be cut so that an area representative of the symmetry of the overall pattern of the deformed region is represented. There will be cases (due to variations in either the size of the deformed portion or the relative geometries of the first and second regions) in which it will be necessary to cut either larger or smaller samples than is suggested herein. In this case, it is very important to note (along with any data reported) the size of the sample, which area of the deformed region it was taken from and preferably include a schematic of the representative area used for the sample. Three separate tests at 20, 60 and 100% strain are typically measured for each material. Three samples of a given material are tested at each percent elongation.

The grips of the Instron consist of air actuated grips designed to concentrate the entire gripping force along a single line perpendicular to the direction of testing stress having one flat surface and an opposing face from which protrudes a half round to minimize slippage of the sample. The distance between the lines of gripping force should be 2" as measured by a steel rule held beside the grips. This distance will be referred to from hereon as the "gauge length". The sample is mounted in the grips with its long axis perpendicular to the direction of applied percent elongation. The crosshead speed is set to 10 in/min. The crosshead moves to the specified maximum percent elongation and holds the sample at this percent elongation for 30 seconds. After the thirty seconds the crosshead returns to its original position (0% elongation) and remains in this position for 60 seconds. The crosshead then returns to the same maximum percent elongation as was used in the first cycle, holds for thirty seconds and then again returns to zero.

A graph of two cycles is generated. A representative graph is shown in FIG. 7. The percent force relaxation is determined by the following calculation of the force data from the first cycle:

$$\frac{\text{Force at Max. \% elongation} - \text{Force after 30 sec. hold} \times 100}{\text{Force at Maximum \% elongation (cycle 1)}} = \% \text{ Force Relaxation}$$

The percent set is the percent elongation of the sample of the second cycle where the sample starts to resist the elongation. The percent set and the percent force relaxation are shown graphically also in FIGS. 7, 9, 11, 13 and 15. The average percent force relaxation and percent set for three samples is reported for each maximum percent elongation value tested.

While the test method described above is useful for many of the web materials of the present invention it is recognized that the test method may have to be modified to accommodate some of the more complex web materials within the scope of the present invention.

Tensile Test

The tensile test is used for measuring force versus percent elongation properties and percent available stretch of a material. The tests are performed on an Instron Model 1122, available from Instron Corporation of Canton, Mass. which is interfaced to a Gateway 2000 486/33 Hz computer available from Gateway 2000 of N. Sioux City, S.D., using TestWorks™ software which is available from Sintech, Inc. of Research Triangle Park, N.C. All essential parameters needed for testing are input in the TestWorks™ software for each test. Also, all data collection, data analysis and graphing are done using the TestWorks™ software.

The samples used for this test are 1" wide×4" long with the long axis of the sample cut parallel to the direction of maximum extensibility of the sample. The sample should be cut with a sharp exacto knife or some suitably sharp cutting device design to cut a precise 1" wide sample. (If there is more than one direction of extensibility of the material, samples should be taken parallel to representative direction of elongation). The sample should be cut so that an area representative of the symmetry of the overall pattern of the deformed region is represented. There will be cases (due to variations in either the size of the deformed portion or the relative geometries of regions 1 and 2) in which it will be necessary to cut either larger or smaller samples than is suggested herein. In this case, it is very important to note (along with any data reported) the size of the sample, which area of the deformed region it was taken from and preferably include a schematic of the representative area used for the sample. Three samples of a given material are tested.

The grips of the Instron consist of air actuated grips designed to concentrate the entire gripping force along a single line perpendicular to the direction of testing stress having one flat surface and an opposing face from which protrudes a half round to minimize slippage of the sample. The distance between the lines of gripping force should be 2" as measured by a steel rule held beside the grips. This distance will be referred to from hereon as the "gauge length". The sample is mounted in the grips with its long axis perpendicular to the direction of applied percent elongation. The crosshead speed is set to 10 in/min. The crosshead elongates the sample until the sample breaks at which point the crosshead stops and returns to its original position (0% elongation).

Graphs of the tensile data are shown in FIGS. 6, 8, 10, 12 and 14. The percent available stretch is the point at which there is an inflection in the force—elongation curve, beyond which point there is a rapid increase in the amount of force required to elongate the sample further. This point is shown graphically in FIGS. 6, 8, 10, 12 and 14. The average of the percent available stretch for three samples is recorded.

While the test method described above is useful for many of the web materials of the present invention it is recognized that the test method may have to be modified to accommodate some of the more complex web materials within the scope of the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A web material exhibiting both an elastic-like and an expansive behavior in response to an applied elongation along at least one axis thereof, said web material comprising:

an elastic-like zone and an expansive zone disposed adjacent to said elastic-like zone, said elastic-like zone comprising a strainable network comprising a first region having a surface-pathlength and a second region having a surface-pathlength, the surface-pathlength of said second region being greater than the surface pathlength of said first region as measured parallel to said axis while said web is in an untensioned condition, said expansive zone having a surface-pathlength greater than the surface-pathlength of said first region and a surface-pathlength different than the surface-pathlength of said second region as measured parallel to said at least one axis while said web is in an untensioned condition.

2. The web material of claim 1, wherein said first region undergoes a substantially molecular-level deformation and said second region intially undergoes a substantially geometric deformation in response to the applied elongation.

3. The web material of claim 2, wherein said expansive zone intially undergoes a substantially geometric deformation in response to the applied elongation.

4. The web material of claim 1, wherein said first region and said second region are visually distinct from one another.

5. The web material of claim 4, wherein said second region comprises a plurality of rib-like elements.

6. The web material of claim 1, wherein said expansive zone comprises a plurality of incrementally stretched regions.

7. The web material of claim 1, wherein said expansive zone comprises with said elastic-like zone.

8. The web material of claim 1, wherein said web material comprises a portion of a disposable absorbent article.

9. The web material of claim 8, wherein said web material comprises a portion of a backsheet on a disposable absorbent article.

10. The web material of claim 1, wherein said web material forms a waist feature on a disposable diaper.

* * * * *